United States Patent [19]

Petersen et al.

[11] 4,106,995

[45] Aug. 15, 1978

[54] MICROORGANISM GROWTH INHIBITOR DEVICE

[75] Inventors: Oscar Johan Petersen, Orange; Timothy Frank Scott, Brea, both of Calif.

[73] Assignee: Robertshaw Controls Company, Richmond, Va.

[21] Appl. No.: 711,489

[22] Filed: Aug. 5, 1976

[51] Int. Cl.² ............................................... C12B 1/20
[52] U.S. Cl. ............................ 195/103.5 R; 195/123; 195/127; 204/195 P
[58] Field of Search ................ 195/103.5 R, 127, 123; 204/195 P; 220/87; 21/2, 58

[56] References Cited

U.S. PATENT DOCUMENTS

| 1,146,714 | 7/1915 | Keen ........................................ 220/87 |
| 1,318,636 | 10/1919 | Wiggins .................................. 220/87 |
| 3,496,084 | 2/1970 | Stack ................................... 204/195 P |
| 3,661,506 | 5/1972 | Watkins ....................................... 21/2 |
| 3,875,036 | 4/1975 | Morris et al. ...................... 204/195 P |

*Primary Examiner*—Alvin E. Tanenholtz
*Assistant Examiner*—C. A. Fan
*Attorney, Agent, or Firm*—Fulwider, Patton, Rieber, Lee & Utecht

[57] ABSTRACT

There is disclosed a device which inhibits the growth of microorganisms on the surface of a primary sensor element, such as the oxygen permeable membrane of a dissolved oxygen cell or the electrode and junction surfaces of a pH cell, immersed in an aqueous culture of the microorganism. The device includes a source of an antiseptic or disinfectant having a slow aqueous dissolution rate that is supported by a carrier having a transport system to sweep the source across the surface to be protected and a drive system to actuate the transport mechanism in a repetitious or a cyclic fashion. In the preferred embodiment the antiseptic source is a copper or heavy metal plate on the end of a blade that is reciprocated across the exposed membrane surface of a dissolved oxygen cell by a spring biased electrical vibrator.

7 Claims, 17 Drawing Figures

U.S. Patent
Aug. 15, 1978
4,106,995
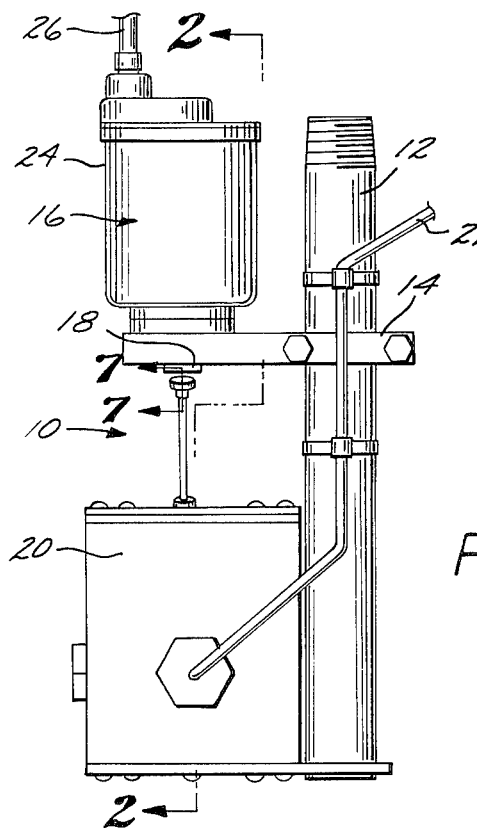
FIG. 1
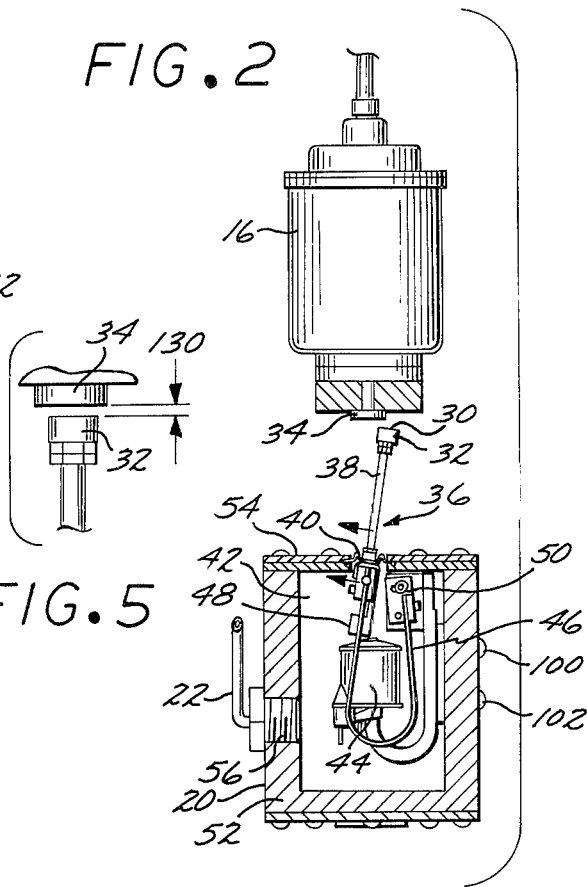
FIG. 2
FIG. 5
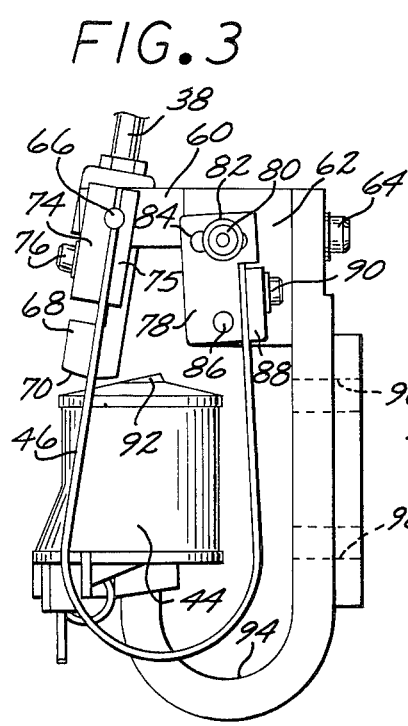
FIG. 3
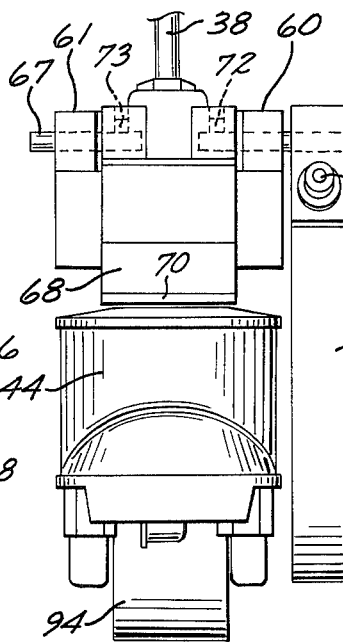
FIG. 4
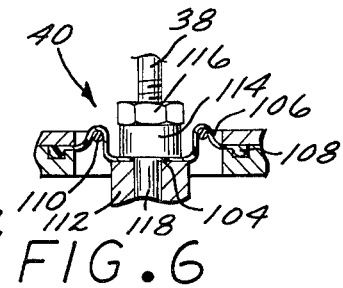
FIG. 6
FIG. 7

MICROORGANISM GROWTH INHIBITOR DEVICE

BACKGROUND OF THE INVENTION

1. Field of the Invention

This invention relates to a device for inhibiting microorganism growth and, in particular, to a device useful to prevent fouling of primary sensing surfaces of analytical instruments.

2. Brief Statement of the Prior Art

Biochemical processes based on the activity of microorganisms frequently employ aqueous media which contain sediment and suspended solids, e.g., an activated sludge process which receives raw sewage streams containing sediment, suspended solids, oils, greases and the like. It is desirable to employ analytical instruments such as dissolved oxygen cells and the like directly in the process streams, thereby avoiding sampling errors inherently associated with streams of this nature.

It has been found that the primary sensor surfaces of analytical instruments when immersed in process streams of this nature rapidly become coated with a deposit of microorganism growth which causes erroneous readings of the instrument.

Various mechanical devices have been proposed for use in combination with analytical instruments such as dissolved oxygen cells, pH cells and the like. Typically these devices comprise agitators to stir the aqueous medium in the vicinity of the sensing surface such as illustrated by U.S. Pat. Nos. 3,498,889 or 3,878,049. Other techniques include apparatus for vibration of the analytical probe containing the oxygen sensing surface such as shown in U.S. Pat. No. 3,869,369. These devices are usually employed to insure that the vicinity of the sensing surface of the analytical probe is continuously replenished with fresh medium, thereby insuring a precise determination of the sensed variable such as dissolved oxygen and the like. When the analytical device is to be employed in a continuous process stream, stagnation of the liquid under analysis seldom occurs and these devices are not employed. The aforementioned devices do not prevent microorganism coatings on the sensing surfaces of process instruments even in rapidly flowing and agitated process streams.

BRIEF DESCRIPTION OF THE INVENTION

This invention comprises a device which is effective in inhibiting microorganism growth on the surfaces of primary sensing elements such as the membranes of dissolved oxygen cells or glass electrode surface or reference junctions of pH cells and the like. The invention comprises a source of an antiseptic or disinfectant which is effective, at low concentrations, in inhibiting the growth of the microorganism. Typically, the invention is directed to biochemical processes which employ bacterial cultures and a source of a bactericide is employed. The invention is equally applicable to various fermentation processes employing yeast cultures and the like.

In the preferred embodiment the source of inhibiting bactericide is a copper plate which slowly releases copper ions to the aqueous stream of microorganism culture. The source of inhibitor is positioned on a carrier which, preferably, is the blade of an agitator that is provided with transport means to drive the carrier and associated inhibitor source across the surface to be protected in a cyclic, reptitious manner. The drive system for the device can be an electrical motor or, preferably, an electrical vibrator having a resilient, spring-biased arm operated by a solenoid.

BRIEF DESCRIPTION OF THE DRAWINGS

The invention will be described with reference to the FIGURES of which:

FIG. 1 is an elevational view of the invention in combination with a dissolved oxygen cell;

FIG. 2 is a view along lines 2—2 of FIG. 1;

FIGS. 3 and 4 are elevational views of the transport means and prime mover used in the invention;

FIG. 5 illustrates the spacing between the protected surface of the primary sensor and the source of antiseptic;

FIG. 6 is a view along lines 6—6 of FIG. 2; and

FIG. 7 is a view along lines 7—7 of FIG. 1.

DESCRIPTION OF PREFERRED EMBODIMENT

Referring now to FIG. 1, the device for inhibition of microorganism growth of the invention is generally indicated as component 10 of the assembly which includes a stand with a conventional pipe column 12 and bracket arm 14 carried thereon and projecting for the support of a primary sensor 16. The primary sensor illustrated is a dissolved oxygen cell which, typically, has an electrode assembly 18 that is exposed to the aqueous medium under investigation such as an aqueous microorganism culture. The entire assembly is intended for submersion in the aqueous medium and, accordingly, the mechanical components of the inhibitor device of the invention are contained within a sealed enclosure 20 which is provided with an electrical conduit 22 that extends to a source of electrical power. The primary sensor such as the dissolved oxygen cell 16 is likewise contained within a sealed enclosure 24 and has a cable 26 containing electrical conductors which extend from the electrodes of the cell.

In FIG. 2, the components of the inhibitory device of the invention are illustrated as including a source of an antiseptic which is a coating 30 on the surface of the carrier means and stirrer paddle 32 which is mounted for sweeping past the surface 34 of the dissolved oxygen cell 16. Typically, surface 34 is a membrane surface and the like which overlies the cathode of a dissolved oxygen cell; the cathode being commonly formed of platinum, gold, silver and the like. The membrane constituting surface 34 is an oxygen permeable film such as a film of from 0.5 to about 5 mills thickness of a plastic such as polyethylene, Teflon, and other suitable plastics.

The transport means for the paddle 32 is generally indicated at 36 and includes the paddle shaft 38 which extends through a flexible annular seal 40 into chamber 42 within the fluid-type enclosure 20. Supported with chamber 42 is the drive means in the form of an electrical prime mover defined by an electromagnet having a coil 44 about a magnetically permeable metal and the like, thereby defining a vibratory motor. The transport means also includes a resilient means such as leaf spring 46 that biases the position of the armature assembly 48 carried at the inboard end of paddle shaft 38 to an offset position such as illustrated in FIG. 2. The leaf spring 46 is mounted in the assembly by a suitable support such as bracket 50.

The enclosure 20 is defined by the cup-shaped member 52 bearing cover plate 54. The electrical conductor 22 extends into chamber 42 through a sealed plug 56.

Referring now to FIGS. 3 and 4, the transport means and drive means employed for the device are shown in greater detail. As there illustrated, the transport means includes pivotal mounting of the armature assembly 48 on arm 60 which is attached to the main frame 62 by machine screw 64. The armature assembly 48 pivots about pin 66 and includes the armature 68 having a pole 70 of a magnetically permeable metal such as soft iron and the like. As illustrated in FIG. 4, the armature mounting bracket has parallel arms 60 and 61 which are bored to receive the pins 66 and 67 for the pivotal mounting of the armature assembly. The pins 66 and 67 are secured to the armature by set screws 72 and 73 which extend through threaded bores in the top surface of the armature member. Shaft 66 extends past the support arm 60 and carries the mounting block 74 for the resilient leaf spring 46. This block is split and receives, between its split halves, the end of leaf spring 46. This assembly is secured by machine screw 76 which extends into threaded engagement with an internally threaded bore in half 75 of the split half block 74.

The opposite end of leaf spring 46 is secured by retainer block 78 that is fixedly attached to the frame 62 by pin 86 and machine screw 80 and lock washer 82. The screw 80 extends through arcuate slot 84 of the retainer block, whereby retainer block 78 can be fixedly adjusted to the support of the assembly. Retainer block 78 removable supports the end of leaf spring 46 with plate 88 and machine screw 90 which extends into threaded engagement with a threaded bore in retainer block 78.

The electromagnet drive motor 44 includes a coil about a core 92 of a magnetically permeable metal such as soft iron and the like. This coil and core subassembly is carried on the end of the U-shaped arm 94 that extends from the block 62. The entire assembly is mounted in chamber 42 with internally threaded bores 96 and 98 in frame 62 that are secured to an internal wall of enclosure 20 by machine screws 100 and 102, shown in FIG. 2.

As previously mentioned, the paddle shaft 38 extends from chamber 42 through seal means 40. The seal means which is employed is a modified, commercially available seal under the designation of Bellofram. This Bellofram seal is a resilient member formed of rubber or other elastomers having a central aperture 104, annular pleat 106 and a circumferential bead 108. The operational life of this seal is vastly improved by the incorporation of the resilient ring 110, similar to an O-ring which is placed within the annular pleat 106 and secured therein by solvent, cement, and the like, thereby imparting strength to the seal member to resist elongational stresses in the direction of the plane of oscillation of the paddle shaft 38. The seal 40 is secured to the armature assembly 48 by the block 112 which has a central bore to receive shaft 118 of pin 114. Shaft 118 is secured by suitable means such as threaded engagement, adhesive engagement, and the like. The end of shaft 38 is threaded and is received within a threaded bore of the head of pin 114 and is secured thereto by lock nut 116.

Referring now to FIG. 7, the paddle 32 is shown in greater detail. As there illustrated, the upper end of shaft 38 is threaded and is received in an internally threaded bore of the paddle blade 120. The paddle blade is secured in the assembly by lock nuts 122 and 124. The upper surface of paddle 126 bears a coating which is the source of antiseptic to inhibit the microorganism growth. In the illustrated and preferred embodiment, this coating is a thin plate 128 of copper, zinc, cadmium, mercury or silver. Preferably, a thin copper plate is employed. This is secured to the upper surface of paddle 126 by an adhesive, brazing and the like.

The paddle 32 carrying the source of the antiseptic material, i.e., the copper plate 128, is mounted for sweeping across the surface of the membrane 34 to be protected. This paddle is mounted such that it remains out of contact with the membrane 34 during this movement and is separated therefrom by a space 130, shown in FIG. 5 which is of sufficient dimension to avoid lodging or trapping of any particles of suspended matter in the aqueous medium. Typically, the aqueous medium in a microorganism culture can contain suspended solid matter such as sand, grit and the like having a particle size up to about 0.05 inch and, accordingly, the clearance dimension 130 which is provided is from 0.01 to about 0.10 inch, sufficient to prevent trapping or clogging of the solid material between the paddle and the membrane.

An apparatus of the type illustrated is employed with a dissolved oxygen cell for determining the oxygen content of a process stream in an activated sludge process. The electromagnetic motor 44 is powered with a 12 volt, 60 Hz alternating current for movement of the armature. A number of experiments are preformed in which the components and/or operation of the inhibitating agitator device are varied. In a first experiment the agitator device is provided with a Teflon paddle having no source of an antiseptic material. This device is operated for eight weeks and it is observed that there is a steadily increasing error in the dissolved oxygen content determinations of the dissolved oxygen meter, reaching 6.6 percent error at the end of the fourth week. At that time the device is removed, the oxygen permeable membrane of the dissolved oxygen cell is cleaned of microorganism growth and the device is reimmersed in the aqueous medium. At the end of the seventh week a 2.9 percent error is observed and the sensor membrane is again wiped clean, the device is reimmersed and at the end of the eight week the readings from the dissolved oxygen cells are in error by an amount of 2.6 percent of the reading.

At the eight week, the Teflon paddle is replaced with a copper clad paddle such as shown in FIG. 7 and the device is reinserted, however, the mechanical agitator is not activated and an error of from 9–12 percent is observed the following week. The sensor membrane is again cleaned and the device is reinserted and operated for a period of four weeks with a cumulative error of only 1.2 percent. The molar concentration of copper in the medium in the locality of the membrane is about $1.0 \times 10^{-7}$, within the range necessary to inhibit bacterial growth. Repeated use of the device as described herein indicates that the device can be employed for periods of many weeks within a tolerance of from 2 to about 3 percent error.

The device has been described with the illustration of the presently preferred embodiment which includes the use of a heavy metal inhibitor for the microorganism growth. It is apparent that other antiseptic materials or disinfectant materials could likewise be employed. Examples of other materials which can be employed include solid iodine and chloride sources, mercury and silver compounds such as mecuric chloride, silver nitrate, phenol mercuric nitrate, phenol mercuric chloride, phenol, resorcinol, hexoresorcinol, etc. Quaternary amonium compounds can also be employed such as alkyl dimethyl benzyl ammonium chloride, cetyl pyridinium chloride, etc.

The aforementioned materials can be employed in limited water solubility or dispersability by incorporating them in a gel or admixing them with an adhesive binder such as latex of polyvinyl alcohol and the like which can be coated on the surface of the paddle and permitted to dry before use. Alternatively, the antiseptic or disinfectant materials can be adsorbed into the pores or on the surface of various adsorptive materials such as molecular sieves, natural and synthetic aluminosilicates such as clays, e.g., montmorillonite, kaolinite, etc., and these solid carriers of the active disinfectant or antiseptic can be coated on the surface of the paddle to provide a slow release material which will remain active over a prolonged or extended life period.

The invention has been described with reference to the presently illustrated and preferred embodiment thereof. It is not intended that the invention be unduly limited by this illustration of presently preferred embodiments. Instead, it is intended that the invention be defined by the means, and their obvious equivalents set forth in the following claims.

What is claimed is:

1. The combination of an oxygen cell having an oxygen permeable membrane for immersion in an aqueous culture of a microorganism and a device for the inhibition of microorganism growth on the surface of said membrane, said device comprising:
    (1) a source of an antiseptic having a limited water solubility sufficient to inhibit microorganism growth in the locality of said membrane but insufficient to inhibit said growth in the main body of said culture;
    (2) carrier means bearing said source;
    (3) transport means for said carrier means to sweep said source carried thereby within said aqueous culture and across said surface of said membrane; and
    (4) drive means to actuate said transport means in a continuous repetitious manner.

2. The device of claim 1 wherein said antiseptic is a heavy metal selected from class of copper, zinc, cadmium and silver.

3. The device of claim 1 wherein said carrier means comprises a blade mounted on an arm pivotally supported opposite said surface to permit movement of said blade across said membrane at a distance from 0.01 to 0.1 inch therefrom.

4. The device of claim 1 wherein said transport means comprises resilient spring means to bias said arm in one direction and solenoid means with armature means operative to move said arm in the opposite direction.

5. A method for inhibiting the growth of microorganisms on the surface of a membrane exposed to an aqueous medium containing said microorganism and dissolved oxygen without substantially inhibiting the activity of said microorganism in said medium which comprises:
    agitating said medium in the vicinity of said membrane to obtain a flow of said medium across said membrane; and
    stirring said medium in the proximity of said membrane with a paddle bearing an exposed surface of a heavy metal microorganism growth inhibitor selected from the class consisting of copper, zinc, cadmium, silver, and mixtures thereof to release a limited amount of said inhibitor sufficient to inhibit microorganism growth in the locality of said membrane but insufficient to inhibit said growth in the main body of said medium.

6. The method of claim 5 including the additional steps of periodically determining the dissolved oxygen content of said medium over a period of time while continuously performing said agitating and stirring steps to inhibit growth of microorganisms on said membrane.

7. The method of claim 6 wherein said paddle is swept across said membrane surface at a distance from 0.01 to 0.10 inch therefrom.

* * * * *